United States Patent [19]

Bashengezi

[11] Patent Number: 5,607,673

[45] Date of Patent: Mar. 4, 1997

[54] PURIFIED EXTRACT OF UVARIA BREVISTIPITATA AND A PROCESS FOR OBTAINING THE PURIFIED EXTRACT THEREFOR

[75] Inventor: Constantin M. Bashengezi, Bukavih, Zaire

[73] Assignee: C.S.S.A.H.A., Inc., Chicago, Ill.

[21] Appl. No.: 425,747

[22] Filed: Apr. 20, 1995

[51] Int. Cl.$^6$ ................................................ A61K 35/78
[52] U.S. Cl. ........................ 424/195.1; 514/885; 514/894; 514/934
[58] Field of Search ...................... 424/195.1; 514/885, 514/894, 934

[56] References Cited

U.S. PATENT DOCUMENTS

| | | |
|---|---|---|
| 4,721,727 | 1/1988 | Kolajczak et al. ....................... 514/473 |
| 4,855,319 | 8/1989 | Kolajczak et al. ....................... 514/473 |
| 5,229,419 | 7/1993 | Win et al. ................................ 514/473 |

OTHER PUBLICATIONS

Jolad, et al, J. Org. Chem. 47:3151–3153, 1982.
Cole, et al., J. Org. Chem. 41:1852–1855, 1976.
Padmaja, et al., J. Ethropharmacol. 40: 181–186, 1993.
Lumonadio, et al., J. Ethropharmacol. 31:59–65, 1991.

*Primary Examiner*—John W. Rollins

[57] ABSTRACT

In HIV infected individuals, certain clinical and biological markers are used to assess the progression or regression of the disease. From the plant, *Uvaria bevistipitata* of the Annonaceae family, a substantially pure extract was derived. This extract was administered to 268 HIV infected patients in a clinical trail in Zaire Africa and dramatic results were obtained. The extract was also submitted to a laboratory for in vitro analysis. when tested against the HIV reverse transcriptase enzyme, the extract tested 96.7% active. In further laboratory analysis, against HIV-$_{IIB}$, it demonstrated efficacy at doses that showed no cytotoxic effects.

14 Claims, 1 Drawing Sheet

1

PURIFIED EXTRACT OF UVARIA BREVISTIPITATA AND A PROCESS FOR OBTAINING THE PURIFIED EXTRACT THEREFOR

BACKGROUND OF THE INVENTION

Purified botanical extracts have long been a source of new and useful pharmaceutical. Plant root extracts from the family Annonaceae have been reported in the literature to have potent cytotoxic and antimicrobial activity. Plants from the family annonaceae, genus Uvaria, have been found to contain compounds such as acetogenins useful as pesticides, and recently as anticarcinogenic agents.

U.S. Pat. No. 5,229,419, discloses such chemo-therapeutically active acetogenins. That invention relates to two acetogenin compounds isolated in substantially pure form from a plant in the Annonaceae family, *Annona bullata* Rich. the two compounds, bullatacin and bullatacinone, were found to exhibit antitumor and pesticidal activity and were characterized as being new members of an unusual class of compounds. The compounds are composed of tetrahydrofuran rings having two adjacent hydroxyl groups.

The starting material for obtaining the purified extracts is the root bark of the *Annona bullata* Rich. plant. Obtaining the purified extracts is performed by standard sterilization and purification processes.

U.S. Pat. No. 4,855,319, discloses an *Annonaceous acetogenin* for the control of pests. In that reference, a new acetogenin called asimicin was extracted from the root bark of a plant from the Annonaceae family. The particular extract was isolated from the plant *Asimina triloba*, also known as the paw paw tree. However, it is noted in that reference that the most potent form of the *Asimina triloba* extract is taken from the bark of the plant, not the root. The extract appears to be a tetrahydrofuranoid fatty acid lactone having variable side chains, however the disclosure is directed to the substantially pure compound, Asimicin.

U.S. Pat. No. 4,721,727, also discloses a purified Annonaceous extract which uses tetrahydrofuranoid acetogenins for controlling pests. That reference is also directed only to use of the compound Asimicin.

Other reported literature has shown that the compound, Uvaricin, taken from the purified root extracts of *Uvaria acuminata*, another Annonaceous plant, demonstrated an in vitro activity against P-388 lymphocytic leukemia in mice. [Jolad, et al., J. Org. Chem., 47:3 151–3153 (1982)]

Another extract, Uvaratin, also from *Uvaria acuminata*, was also shown to have anti-tumor activity. [Cole, et al., J. Org. Chem 41 (10)pp. 1852–1855, (1976)].

In fact, the literature contains numerous reports that plant extracts from the Annonaceae family have been investigated for their medicinal and toxicological effects. In one pharmacological screening, substantial antibacterial, antifungal, and anthelminthic activities were observed using extracts of the root barks of Uvaria Narum Wall, and Uvaria Hookeri king. [Padmaja et al., J. Ethnopharmacol (IRELAND), 40(3) pp. 181–186 (December, 1993)].

In another study, species from Uvaria originating from Tanzanian plants were tested for their in vitro activity against the multi-drug resistant K 1 strain of plasmodium falciparum, the causative agent for the disease malaria. In this study, root extracts from the stem and root barks, of *Uvaria lucida* and Uvaria sp. (pande), were reported as having anti-malarial activity. Among the compounds isolated in this study were Uvaretin, Diuveretin, and 8',9'-dihydroxy-3-farnesylindole as the most active compounds. The particular Uvaria species consisted of nine varieties from Tanzania and included: *U. dependens, U. faulknerae, U. kirkii, U. leptocaldon, U. lucida*, Uvaria sp. (Pande), *U. scheffieri*, and *U. tanzaniae*. [Nkunya et al., Planta Med, 57 (4) pp. 341–3, (1991)].

Yet another species, *Uvaria chamae*, has also been reported to have anti-microbial activities. In that study, cytotoxic C-benzylated flavonoids exhibited anti-microbial inhibition which compared favorably to that of streptomycin sulfate, an inhibitor of protein synthesis. [Hufford, et al., J. Art., 41 (2) pp. 156–60, (1978)]. However, compounds taken from the roots of *Uvaria chamai* has also been implicated as a causative agent for liver cancer. Two separate studies out of sub-Saharan Africa have shown that the active compound in *Uvaria chamaii*, chamuvaritin, has shown that it has mutagenic effects. One of the studies also showed that sub-Saharan Africa is a high incidence area for hepatocellular carcinoma. Although the disease is multi-factorial in etiology, including a combination of causative agents such as Hepatitis B Virus, and chemical carcinogens, the compounds contained in the medicinal plants were implicated as potential sources of causative agents for liver cancer. [Uwaifo, et al., IARC Sci. Publ., 63 pp. 59–88 (1984). (Uwaifo, et al., Cancer Lett, 8 (1) pp. 87–92 (1972)].

In addition to the cytotoxic, antitumor, and antimicrobial activities of plant extracts from the Annonaceae family, other root bark extracts are reported in the literature as having medicinal purposes. One compound, 15-desacetylundulatone, a quassinoid, was found active against P-388 mouse lymphocytic leukemia cells and Colon-38 adenocarcinoma. [Lumonadio et al., J. Ethnopharmacol., 31 (1) pp. 59–65, (SWITZERLAND) (January, 1991)].

Prior literature has also reported root bark extracts capable of anti-viral activity. An anti-Herpes virus compound was purified from the root bark extract of the citrus plant (Rutaceae). [Yamamoto et al., J. Antiviral Res., 12(1) pp. 21–36, (NETHERLANDS) (August, 1989)]. In that study, the compound exhibited potent activity against Herpes Simplex Virus Type 1 (HSV-1) and Herpes Simplex Virus Type 2 (HSV-2) at low concentrations relative to their cytotoxicity. Additionally, the compound was also shown to suppress Cytomegalovirus (CMV), another member of the Herpes virus family.

Although the exact mechanism of action of root bark compounds taken from the Annonaceae family is not known, two recent articles may provide some insight. Annonaceous acetogenins, natural products from the plants described above, were shown to be very potent inhibitors of the NADH-Ubiquinone Reductase (Complex I) activity of mammalian mitochondria, and exhibit a high potential for interfering with the production of energy within mammalian cells. The acetogenins, Rolliniastatin-1 and Rolliniastatin-2, were compared against classical inhibitors of Complex I and were shown to be more powerful in terms of both their inhibitory constant and the protein dependence of their titer in bovine submitochondrial particles. Although the above results only apply to Rolliniastatin-1 and Rolliniastatin-2, Squamocin and Otivarin also showed an inhibitory constant lower than that of the classical inhibitor. [Degli, et al., Bio. Chem. J, 301 (Pt. 1) pp. 161–7, (1994)].

Another potential mechanism of action may be similar to that of Annonaceous alkaloids. These compounds show a selective toxicity against DNA repair and recombination-deficient mutants of the yeast. *Saccharomyces cerevesie*.

[Harrigan, et al., J. Nat. Prod., 57 (1) pp. 68–73, ( 1994)]. However, Herpes viruses have large genomes consisting of double-stranded DNA and dedicated viral machinery for DNA synthesis. Thus, the inherent structure double-stranded DNA viruses, like those of the Herpes virus family, will provide treatments which may only be effective against viruses of the same family.

However, there is no reference in the literature reporting that the use of plant root extracts or compounds generated from the family Annonaceae would be efficacious in an anti-viral capacity. Further, there is no reference in the prior art that a plant extract from the Uvaria genus of the Annonaceae family may be useful in an antiviral capacity. As an antineoplastic agent, or as a treatment for diseases caused by immunodeficiency.

SUMMARY OF THE INVENTION

The present invention disclosed herein consists of a novel purified extract of the plant Uvaria brevistipitata of the Annonaceae family, a process of using such an extract for the treatment of vital or immunodeficiency diseases, and a novel process for the purification and extraction of such a plant extract.

In a preferred embodiment, the purified extract is obtained from the Uvaria brevistipitata plant through a simple but effective laboratory process which purifies and concentrates the active compound. This process may be accomplished with standard laboratory equipment and it is efficient in both cost and labor.

In one preferred embodiment, the process of treating persons with the purified extract for a vital or immunodeficiency disease may be obtained by encapsulating the dried extract in 300 mg capsules in a process detailed herein. These capsules are then administered over approximately 6 months according to the regimen detailed herein. In laboratory analysis, in vitro, the extract exhibited non-cytotoxic antiviral effects when tested against HIV-$_{IIIB}$. The anti-viral effects were seen at concentrations of 0.7 mg/mL, 1.4 mg/mL, 2 mg/ml, and at 3 mg/ml. Further, when tested in vitro against the HIV reverse transcriptise enzyme, the extract demonstrated 96.7% active. The near purified extract was used in a human clinical study in Zaire, Africa, in which 268 subjects were administered the purified extract over a period of one to six months. The subjects were selected according to symptoms consistent with Acquired Immune Deficiency Syndrome (AIDS) and the results indicate a symptomatic remission of the disease in over 60% of the subjects. Additionally, the process of treating persons with the purified extract is very simple and cost effective.

A preferred embodiment of the purification and extraction process described herein is also very simple and cost effective to utilize with basic laboratory equipment. The purification and extraction process consists of an extraction step, a purification step, a concentration step, and a drying step. The extraction step consists of taking root bark portions of the plant and grinding or pulverizing them to an appropriate size and consistency. The purification step consists of taking a large quantity of ground root, boiling the ground root in distilled water, adding activated carbon to the mixture, cooling the mixture for a period of time, filtering the treated root, and collecting the filtrate. The concentration step consists of taking the treated filtrate and subjecting it to distillation under heat until a (soft viscous extract is formed as a result.) The drying step consists of grinding the extract in a mortar and pestle in the presence of a drying agent, and placing the ground extract in a dryer of 45° C. until dry. None of the foregoing requires expensive laboratory equipment to accomplish the intended purpose.

OBJECTS OF THE INVENTION

Thus, it is an object of this invention to provide an extract from an Annonaceous plant, Uvaria brevistipitata, in substantially pure form utilizing a standard laboratory process of extraction, purification, concentration and drying.

It is another object of the present invention to provide compounds derived from the root bark of Uvaria brevistipitata useful against diseases characterized by immunodeficiency, such as Acquired Immune Deficiency Syndrome (AIDS).

It is another object of the present invention to provide a process for purifying useful compounds from root bark extracts of Uvaria brevistipitata such that said process can be performed in a basic laboratory in a cost effective manner.

It is another object of the present invention to provide anti-vital compounds derived from Uvaria brevistipitata as a new pharmacological treatment for patients having low CD4 counts characteristic of immunodeficiency diseases.

It is another object of the present invention to provide anti-vital compounds derived from purified plant extracts of plants from the family, Annonaceae, which are produced in a cost efficient manner using standard laboratory and pharmacology equipment.

Other objects and advantages of the invention will become apparent to those of ordinary skill in the art upon review of the following detailed description, claims, tables, and charts disclosed herein.

DETAILED DESCRIPTION OF THE PREFERRED EMBODIMENTS

Figure 1:
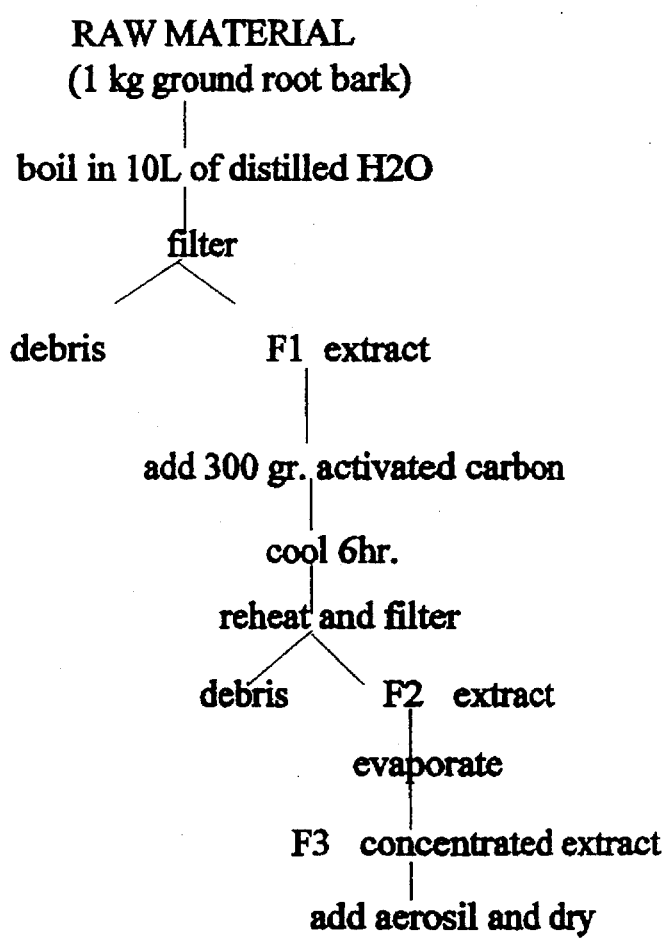
FIG. 1 is a flow chart showing the process comprising the steps of extraction, purification, concentration, and drying to form the inventive compound.

The invention consists of a substantially purified novel root extract obtained from a plant of the family Annonaceae, genus Uvaria, and the process for the obtaining of the novel extract from the plant's natural state for use as a treatment against viral and immunodeficiency caused diseases. In a preferred embodiment, the plant used is the Uvaria brevistipitata plant. The substantially purified root extract is described herein chemically and through the processes of extraction detailed in the examples that follow. The use of the novel extract as a treatment against viral and immunodeficiency caused diseases is described herein by way of the clinical findings detailed in the Tables and their associated descriptions.

In a preferred embodiment, a substantially purified root extract was taken from the plant Uvaria brevistipitata in a clinical study conducted in Zaire, Africa. The substantially purified extract in the study was called UM-127. The substantially purified Uvaria extract, UM-127 contains various saponins, catechic tannins, amine components, and reductor components. Although the specific chemical or composition of chemicals found within the Uvaria extract have not been determined conclusively, it is thought that the active ingredients are found within the amine components of the extract. However, this should not be taken to limit the scope of the invention or to be exclusive of chemicals found with the Uvaria extract having active properties for the uses described herein. The results of Table 1 are derived from conventional combustion analysis known to those skilled in the art and are described using conventional chemical notations known to those skilled in the relevant arts.

TABLE I

| AMINE COMPONENTS IN PURE U.M. - 127 | | | |
|---|---|---|---|
| ASHES | ELEMENTS | PPM | % |
| 0.06 GR | Na | 15.452 | 2.58% |
| | Fe | 2.0 | 0.30% |
| | K | 111.429 | 18.58% |
| | Ca | 34.25 | 5.71% |
| | Cu | 0 | 0 |
| | Mn | 0.442 | 0.07% |
| | Co | 0 | 0 |
| | Mg | 15.545 | 2.59% |
| | P | 39.375 | 6.56% |
| | TOTAL | | 36.394% |

The toxicity of U.M.-127 is shown in Table 2. The toxicity factors include the Lethal Dosage wherein 50% of subjects would suffer lethal consequences (LD 50), the therapeutic index, the subacute toxicity, and the therapeutic dosage adopted based on a 60 kilogram adult. The above terms are defined as would be known to those skilled in the art. However, generally speaking, the toxicity factor, LD 50, is conventionally given as a murine mortality figure (rat studies) when human subjects are used in a study. The therapeutic dosage adopted is the amount given to a particular person, here 60 kilograms, as a ratio of the body weight per day of treatment. The therapeutic index provides a normalized value based on body weight or body surface area such that a therapeutic value may be calculated for a particular individual. The subacute toxicity concerns the level at which non-immediate, chronic health problems may arise during a particular treatment regimen. Table II addresses the values from the study at hand.

TABLE II

TOXICITY

LD 50 - 0,68526 g/kg/day
THERAPEUTIC DOSAGE ADOPTED: 60 kg ADULT = 0,035 g/kg/day
THERAPEUTIC INDEX = 19,57
SUBACUTE TOXICITY: NIL AT 0,608 mg/g/day dosage Accordingly, clinical data is provided describing the results of a treatment utilizing UM-127 in patients exhibiting various diseases and symptoms such as those found in patients having Acquired Immune Deficiency Syndrome (AIDS). The clinical study occurred in Zaire, Africa, and documented results obtained from a treatment given to 268 patients. The patients were chosen based on the criteria shown in Table III below.

UM-127: Clinical Trails

The criteria of the clinical trials in Table III includes the criteria for the recruitment of the subjects and the criteria by which the progress of the subjects would be measured. The L.T4(CD4) count refers to the level of lymphocytic T4 cells in a particular individual. Without discussing the entire role of T4 cells in the human immune system, it should be adequate for a person skilled in the art to recognize that T4 cells are the "T" lymphocytes which contain the receptor molecule CD4 and which is the particular receptor which binds HIV. Accordingly, it is know that a low level of T4 cells is indicative of HIV infection and of an inability to mount immune responses to secondary infections.

TABLE III

RECRUITMENT CRITERIA

Being voluntary
Being HIV +, Western Blot confirmed
Having L.T4 (CD4) $\leq$ 450 by mm$^3$ of serum
Having a Banqui score of 12
Having been received between 02/17/1988 (February 17, 1988) and 11/05/1988 (November 5, 1988)
Having a minimum of 30 day treatment period The criteria by which the subjects were followed through the study included those criteria listed in Table IV below. Farget symptoms are those symptoms listed which have been indicated as being associated with a diagnosis of Acquired Immune Disease syndrome (AIDS). The weight of the individual is an important factor due to the extreme weight loss suffered by patients infected with HIV. White globule count (lymphocyte count), sedimentation speed i.e. the rate at which red blood cells separate from blood serum in a column, hemoglobin rate, and lymphocytic screening are all conventional tests performed in a hematology laboratory for the purposes of determining the progression of the clinical status of an individual.

TABLE IV

CRITERIA OF BIO-CLINICAL EVOLUTION

Farget symptoms: fatigue, lace of appetite, diarrhea, fever
Weight
White globule count
Sedimentation speed
Hemoglobin rate
Lymphocytic screening The patients in the study were classified according to Center for Disease Control (C.D.C.) Classifications, which are herein incorporated by reference. Table V shows that of the 268 subjects enrolled in the study, 5.6% were Group II and 94.4% were Group IV. Table V also shows the breakdown of Group IV into its sub-classifications by raw score and percentage and shows the number of males and females enrolled. 125 and 143 respectively, and the mean age of the participants, 36 and 30 respectively.

TABLE V

PATIENTS

TYPE OF HIV INFECTION (C.D.C. CLASSIFICATION) GROUP IV

| PATIENTS | | GROUP | | | | | AGE | |
|---|---|---|---|---|---|---|---|---|
| M | F | II | S/GR.A | S/GR.B | S/GR.C | S/GR.D | M | F |
| 125 (46.6%) | 143 (53.4%) | 15 | 100 | 18 | 115 | 20 | | |
| 26 | 8 | 5.6% | 37.3% | 6.7% | 42.9% | 7.5% | 36 | 30 |

Table VI shows the clinical evolution of the subjects according to five catagories. The catagories were: 1. Improved and reinstated; 2. Improved and still in need of continued treatment; 3. Asymptomatic; Group II; 4. Clinical Status Quo; and 5. Dead

TABLE VI

CLINICAL EVOLUTION

| CLINICAL EVOLUTION | | NUMBER | DURATION OF TREATMENT (MONTHS) | | | | | |
|---|---|---|---|---|---|---|---|---|
| | | | 1 | 2 | 3 | 3–6 | 6–12 | >12 |
| IMPROVED AND REINSTATED | REGULARLY WATCHED | 57 | 1 | 6 | 12 | 19 | 10 | 9 |
| | UNSEEN | 28 | 1 | 5 | 13 | 8 | 1 | 0 |
| | TOTAL | 85 (31.7%) | 2 | 11 | 25 | 27 | 11 | 9 |
| IMPROVED STILL IN NEED OF CONTINUATION OF TREATMENT | REGULARLY WATCHED | 25 | 7 | 6 | 1 | 7 | 0 | 4 |
| | UNSEEN | 54 | 6 | 24 | 15 | 7 | 2 | 0 |
| | TOTAL | 79 (29.5%) | 13 | 30 | 16 | 14 | 2 | 4 |
| ASYMPTOMATIC GROUP II | | 15 (5.6%) | 3 | 3 | 9 | 0 | 0 | 0 |
| CLINICAL STATUS QUO | REGULARLY WATCHED | 7 | 3 | 0 | 1 | 2 | 0 | 1 |
| | UNSEEN | 14 | 1 | 3 | 5 | 4 | 1 | 0 |
| | TOTAL | 21 (7.8%) | 4 | 3 | 6 | 6 | 1 | 1 |
| DEAD | REGULARLY WATCHED | 31 | 6 | 4 | 3 | 10 | 5 | 3 |
| | UNSEEN | 38 | 0 | 3 | 16 | 12 | 2 | 5 |
| | TOTAL | 69 (25.7%) | 6 | 7 | 19 | 22 | 7 | 8 |

DURATION OF TREATMENT: MINIMUM = 1 MONTH, MAXIMUM = 30 MONTHS

Table VII shows the causes of stagnation for the twenty subjects listed in 4. clinical status Quo in table VI. The four categories of causes of stagnation include the opportunistic diseases: 1. grave lung diseases i.e. pneumonia: 2. acute hydro-electrolytic troubles: 3. kaposi's Sarcoma, a type of cancer having mesodermal origin and seen in AIDS patients; 4. Neurologic illnesses

TABLE VII

CAUSES OF STAGNATION WITHIN THE 21 PATIENTS

| DOMINANT OPPORTUNISTIC ILLNESS | NUMBER | PERCENT |
|---|---|---|
| 1. Grave Lung Illiness | 10 | 47.6% |
| 2. Acute Hydro-Electrolytic Troubles | 5 | 23.8% |
| 3. Kaposi Sarcoma | 4 | 19.0% |
| 4. Neurologic Illnesses | 2 | 9.5% |

The causes of death for the sixty nine patients listed as dead in table IV is given according to the dominant opportunistic illness in table VIII below. The opportunistic illinesses are as follows: Grave Lung illness i.e. *Pneumocystic carnii* Pneumonia; acute hydro-electrolytic troubles; generalized Kaposi's Sarcoma; Neurological illness; Recurring Zona; and other opportununistic illiness. It should be noted, however, of the 69 patients admitted to the study who died, 53 of them, or 76.8% had L. T4 (CD4) counts of less than or equal to 10 on admission. Thus, many of those who died had extremely low lymphocyte counts on admission to the study and as such it cannot be said whether the treatment had conclusive effect on those patients.

TABLE VIII

CAUSES OF DEATH FOR THE 69 PATIENTS

| DOMINANT OPPORTUNIST ILLNESS | NUMBER | PERCENT |
|---|---|---|
| GRAVE LUNG ILLNESS (PCP) | 28 | 40.6% |
| ACUTE HYDRO-ELECTROLYTIC TROUBLES | 21 | 30.4% |
| GENERALIZED KAPOSI SARCOMA | 9 | 13.0% |
| NEUROLOGICAL ILLNESS | 8 | 11.6% |
| RECURRING ZONA | 2 | 2.9% |
| OTHER | 1 | 1.5% |

Patients regularly weighed, 40.6% gained 2 to 6 kg. 14.4% gained 6 to 10 kg, and 17.5% gained over 10 kg as shown in table IX. Since weight loss is a significant problem in patients suffering from AIDS, the results indicate a remission and reversal of this symptom in a majority of the patients tested.

TABLE IX

WEIGHT GAIN FOR 116 PATIENTS REGULARLY WEIGHTED

| SAMPLE POPULATION | WEIGHT GAIN INTERVAL | PATIENTS NUMBER | PERCENT |
|---|---|---|---|
| 160 | GAIN OF 2 TO 6 KG | 65 | 40.6% |
|  | GAIN OF 6 TO 10 KG | 23 | 14.4% |
|  | GAIN OF MORE THAN 10 KG | 28 | 17.5% |

Maximum gain: 30 kg

The following table shows just how effective the treatment is in regard to a quick remission of symptoms found in AIDS patients. Table X shows how the treatment elliminated virus induced fever in the first week by 93.9%, stopped weight loss within ten percent in 74.2% of cases, increased appetite by the fifth day in 92.4% of cases, gave a feeling of well being in 95.7% of cases, and eliminated or reduced skin rash in 67.5% of cases. Table XI and Table XII show how well the symptomatic reduction of the treatment is by considering all of the symptoms in a two by two and three by three mannor. Table XIII shows that when all of the symptoms are taken together, the treatment still yields a 59.5% improvement rate in the clinical population as a whole. Table XIV shows the undesirable side effects of treatment occurring as polyuria in 26.8% of patients treated.

TABLE X

FARGET SYMPTOMS TAKEN ALONE (ONE BY ONE)

| FARGET SYMPTOMS | COMPLAINING POPULATION | IMPROVED POPULATION | PERCENT |
|---|---|---|---|
| 1. Virus-induced fever: 1st week | 149 (58.9%) | 140 | 93.9% |
| 2. Lack of weight ≧ 10% | 225 (88.9%) | 167 | 74.2% |
| 3. Fatigue: 1st week | 208 (82.2%) | 187 | 89.9% |
| 4. Diarrhea ≧ 30 days: 1st 10 days | 82 (32.4%) | 63 | 76.8% |
| 5. Appetite; 5th day | 172 (68.0%) | 159 | 92.4% |
| 6. Recovery of well-being feeling | 253 (94.4%) | 242 | 95.7% |
| 7. End of reduction of skin rash | 220 (82.1%) | 181 | 67.5% |

TABLE XI

FARGET SYMPTOMS TAKEN 2 BY 2

| FARGET SYMPTOMS | COMPLAINING POPULATION | IMPROVED POPULATION | PERCENT |
|---|---|---|---|
| 1. Lack of weight and fatigue | 131 (51.8%) | 125 | 95.4% |
| 2. Diarrhea & lack of weight | 43 (17.0%) | 40 | 93.0% |
| 3. Lack of weight and Anorexy | 101 (40.0%) | 98 | 97.2% |
| 4. diarrhea & Fatigue | 47 ((18.6%) | 44 | 93.6% |
| 5. Fatigue & Anorexy | 126 (49.8%) | 102 | 80.9% |

TABLE XII

FARGET SYMPTOMS TAKEN 3 BY 3

| FARGET SYMPTOMS | COMPLAINING POPULATION | IMPROVED POPULATION | PERCENT |
|---|---|---|---|
| 1. Fever & lack of Weight & fatigue | 93 (36.8%) | 90 | 96.8% |
| 2. Fever & Diarrhea & Lack of Weight | 37 (14.6%) | 35 | 94.6% |
| 3. Fever & lack of Weight & Anorexy | 71 (28.1%) | 67 | 94.4% |
| 4. Diarrhea & Lack of Weight & Anorexy | 30 (11.9%) | 28 | 93.3% |
| 5. Diarrhea & Fatigue & Anorexy | 36 (14.2%) | 32 | 88.9% |

TABLE XIII

FARGET SYMPTOMS TAKEN ALL TOGETHER

| FARGET SYMPTOMS | COMPLAINING POPULATION | IMPROVED POPULATION | PERCENT |
|---|---|---|---|
| Fever & Diarrhea & lack of Weighr & Fatighe & anorexy | 42 (16.6%) | 25 | 59.5% |

TABLE XIV

UNDESIRABLE REACTIONS

| POLYURIA WITHIN 72 PATIENTS | (26.8%) |
|---|---|

Biological Examination

Table XV shows the increase in CD4 counts for patients in the study. Table XV shows how patients entered the study having CD4 counts below 100 and those having CD4 counts between 100 and 450 showing an increase in 75.9% of cases. The cases that started below 100 had an increase of 326.3% and the cases that started between 100 and 450 had an increase of 200% as shown in table XV below. Further table XVI shows how patients had an overall increase in their total lymphocyte levels.

TABLE XV

EVOLUTION OF LYMPHOCYTES RATES
Patients with CD4 (L.T4) ≦ 100 and
100 > CD4 ≦ 450 having improved their rates of CD4

| PATIENTS/ CD4 | SAMPLE POPULATION | IMPROVED POPULATION | PERCENT | MOYEN RATES OF INCREASING |
|---|---|---|---|---|
| CD ≦ 100 | 25 | 18 | 72.0% | 326.3% |
| CD4 > 100 ≦ 450 | 87 | 67 | 77.0% | 200.0% |
| TOTAL | 112 | 85 | 75.9% | |

TABLE XVI

NUMBER OF PATIENTS HAVING IMPROVED THEIR RATES OF L. TOTAL (CD)

| | CD ≦ 1500/mm$^3$ on admission | CD > 1500/mm$^3$ on admission | TOTAL |
|---|---|---|---|
| SAMPLE POPULATION | 20 | 69 | 89 |
| (SCORE) IMPROVED POPULATION | 15 | 55 | 70 |
| PERCENTAGE | 75.0% | 79.7% | 78.7% |

Table XVII shows the increase of hemoglobin rates for 85 patients enrolled in the study from admission to after treatment. Those patients who began the treatment having a hemoglobin below or equal to 7.5 increased to above 9.5 in 71.4% of cases, those entering between 7.5 and 9,5 showed an increase to above 9.5 in 64.3% of cases and those starting above 9.5 ended treatment above 9.5 in 92.2% of cases. Thus, in 85.9% of cases patients in treatment ended the treatment having a hemoglobin above 9.5.

TABLE XVII

EVOLUTION OF HEMOGLOBIN RATES WITHIN 85 PATIENTS

| Hgb count<br>Hgb admission | NUMBER | Hgb ≤ 7.5 | >7.5 Hgb<br>≤ 9.5 | Hgb<br>> 9.5 | MOYENNE<br>Hgb count |
|---|---|---|---|---|---|
| Hgb adm. ≤ 7.5 | 7 | 1 | 1 | 5 | 10.3 |
| Moyenne Hgb adm = 7.0 | (100%) | (14.3%) | (14.3%) | (71.4%) | |
| >7.5 Hgb adm ≤ 9.5 | 14 | 0 | 5 | 9 | 10.5 |
| Moyenne Hgb adm = 8.6 | (100%) | (0.0%) | (35.7%) | (64.3%) | |
| Hgb adm. > 9.5 | 64 | 2 | 3 | 59 | 11.4 |
| Moyenne Hgb adm = 11.9 | (100%) | (3.1%) | (4.7%) | (92.2%) | |
| TOTAL | 85 | 3 | 9 | 73 | |
|  | (100%) | 3.5% | (10.6) | 85.9% | |

Table XVIII shows how 8 patients had an increase in their sedimentation rate over the course of the treatment.

TABLE XVIII

EVOLUTION OF BLOOD SEDIMENTATION SPEED (V.S) WITHIN PATIENTS

| V.S count<br>V.S Admission | NUMBER | V.S. ≤ 20 | >20 V.S ≤ 40 | V.S > 40 | V.S Count<br>MOYENNE |
|---|---|---|---|---|---|
| V.S Adm ≤ 20 | 21 | 11 | 5 | 5 | 27.6 |
| V.S Adm Moyenne = 11.2 | (100%) | (52.4%) | (23.8%) | (23.8%) | |
| >20 V.S Adm ≤ 40 | 11 | 2 | 1 | 8 | 36.5 |
|  | (100%) | (18.2%) | (9.1%) | (72.7%) | |
| V.S Adm Moyenne = 30.8 |  |  |  |  |  |
| V.S Adm > 40 | 55 | 10 | 18 | 27 | 51.7 |
| V.S Adm Moyenne = 75.7 | (100%) | (***) | (32.7%) | (49.1%) | |
| TOTAL | 87 | 23 | 24 | 40 | |
| PERCENTAGE | 100.0% | 26.4% | 27.6% | 46.0% | |

EXAMPLES OF PURIFICATIONS AND EXTRACTION PROCESSES

Accordingly, the process of obtaining the purified extract of *Uvaria brevistipitata* is given by way of example below. The process contains four conventional steps; extraction, purification, concentration, and drying. The process is simply and easily performed in a standard laboratory with a minimum of processing equipment.

The following examples are intended only to further illustrate the invention and are not intended to limit the scope of the invention which is defined by the claims herein.

Example 1

Referring to FIG. 1, in a preferred embodiment, the extraction step begins with taking one kilogram (1 Kg.) of ground root of *Uvaria brevistipitata* 11. This plant is part of the Annonaceae family and is found primarily in Zaire, Africa, although members of the Annonaceae family grow in many tropical regions around the world. The extraction consists of grinding the root 12 to a substantially fine consistency such that the fibers of the root are reduced and the plant root cell wall is substantially disrupted. The grinding is performed using a conventional grinding apparatus or mill and results in a finely ground powder consisting of particles having a diameter in the approximate range of 0.001 mm to 5,000 mm.

The purification step consists of adding 1 kg ground root to approximately ten liters (10 L.) of distilled water and boiling it for a period of approximately 30 minutes 13. To this mixture is then added 300 gr. of activated carbon to remove impurities 14. The activated carbon functions to bind charged molecules and deionize the solution by removing metabolites and ions from the solution. Thus, the activated carbon functions to purify the solution by absorption. The mixture is then allowed to cool for approximately three (3) hours 15. This treated mixture is then filtered using either Watman's filter paper no. 1, or it may be poured through a funnel where the mouth of the funnel has been filled with ordinary cotton 16.

The concentration step consists of collecting the filtrate which is the brownish liquid which dripped through the funnel. This liquid is then distilled until a high concentration of filtrate is obtained 17. the device used to distill the filtrate under heat is a rotary evaporator, which is known in the relative field of laboratory chemistry and pharmacology and is readily available in the marketplace. A preferred temperature for the heated distillation process is between 40° C.–50° C. The concentrated filtrate is allowed to cool for approximately two (2) hours. When cooled, there precipitates a white-yellowish gelatinous, and highly viscous in substance. This substance is the extract which contains the active compound(s). The filtrate is then filtered 19 and this extract is collected from the filter media 21 for drying. To expedite the precipitation process of the active compounds, approximately ½ liter of methanol is added to the concentrated filtrate 18.

The final process consists of a drying step which is utilized to dry the purified concentrated compound for preparation into a fine powder suitable for use in capsules. In this process, the process consists of adding a drying agent 22 to the extract, grinding the extract into a fine paste in a mortar and pestle 23, and drying the ground extract in a dryer 24. In a preferred embodiment, the purified, concentrated compound is mixed with approximately 20 grams of Aerosil 200 powder. The extract and powder are ground together in a mortar and pestle until the extract is no longer viscous and will not stick to either the pestle or the mortar. The dried extract is placed in a dryer at 45° C. until completely dry. The dry extract is then ground until it becomes a fine powder.

Example 2

In this preferred embodiment, obtaining a purified extract consists of an extraction/filtration step, a concentration step, and a drying step. The extraction step begins with taking one kilogram (1 Kg.) of the ground root of *Uvaria brevistipitata* and grinding the root to a substantially fine consistency such that the fibers of the root are reduced and the plant root cell wall is substantially disrupted. The grinding is again performed using a conventional grinding apparatus or mill resulting in a finely ground powder consisting of particles having a diameter in the approximate range of 0.001 mm to 5.000 mm. The ground root is then added to 10 liters of boiling distilled water and boiled for approximately 30 minutes. The solution is then filtered while still hot using absorbent cotton gauze and filter to remove macroscopic cell debris. The filtrate (F1) is then collected and concentrated by distillation under increased temperature in a heated distillary at approximately 45° C.–50° C.

The concentration step consists of subjecting approximately 3 liters of the filtrate (F1) to an evaporation consisting of distillation under reduced pressure and increased temperature, 40° C., until a soft viscous extract results.

The drying step in this example consists of adding a drying agent to the viscous extract, grinding the extract into a fine paste in a mortar and pestle, and drying the ground extract in a dryer. In a preferred embodiment, the extract (F2) is mixed with approximately 20 grams of Aerosil 200 powder. The extract and powder are ground together in a mortar and pestle until the extract is no longer viscous and will not stick to either the pestle or the mortar. The dried extract is then placed in a dryer at 45° C. until completely dry. The dry extract is then ground until it becomes a fine powder.

Example 3

In this preferred embodiment, obtaining a purified extract consists of an extraction step, a purification step, a concentration step, and a drying step. The extraction step begins with taking one kilogram (1 Kg.) of the ground root of *Uvaria brevistipitata* and grinding the root to a substantially fine consistency such that the fibers of the root are reduced and the plant root cell wall is substantially disrupted. The grinding is performed using a conventional grinding apparatus or mill resulting in finely ground paste consisting of particles having a diameter in the approximate range of 0.001 mm to 5.000 mm.

The purification step consists of adding the ground root to a volume of boiling distilled water which contains activated carbon and filtering the mixture. In a preferred embodiment of the invention, 10 liters of distilled water are used per 1.0 kilo of root as starting material. The ground root is added to the distilled water along with 300 grams of activated carbon. The activated carbon functions to bind charged molecules and deionize the solution by removing metabolites and ions from the solution. Thus, the activated carbon functions to purify the solution by adsorption. The solution is boiled for approximately thirty minutes and left to stand until cool to the touch, or approximately 3 hours. When the solution has cooled, the resulting solution is filtered. The filtration consists of using Watmans Filter Paper No. 1, however other appropriate types of sizes of filter paper and filtering devices may be substituted. The filtrate (F2) is collected and concentrated by heated distillation, i.e. Rotary Evaporator, at 45° C.–50° C.

The concentration step consists subjecting approximately 3 liters of the filtrate (F1) to an evaporation protocol consisting of distillation under reduced pressure and increased temperature, 40° C., until a soft viscous extract results.

The drying step in this example consists of adding a drying agent to the viscous extract, grinding the extract into a fine powder in a mortar and pestle, and drying the ground extract in a dryer. In a preferred embodiment, the extract (F2) is mixed with approximately 20 grams of Aerosil 200 powder. The extract and powder are ground together in a mortar and pestle until the extract is no longer viscous and will not stick to either the pestle or the mortar. The dried extract is then placed in a dryer at 45° C. until completely dry. The dry extract is then ground until it becomes a fine powder.

Example 4

In another embodiment, the dried extract may be obtained as follows: according to a method entitled herein as "Constantin's Method", 1.0 kg of ground root is added to 1.0 liter of boiling distilled water. To this mixture is added 100 grams of activated carbon. The root-water-carbon mixture is boiled ½ an hour. After boiling, the mixture is filtered using ordinary cotton and left to sit until the filtrate becomes white which takes approximately two hours. After this time, the mixture is filtered using Watman's No. 1 size filter paper. The resultant filtrate is allowed to stand about two hours where it cools. During this time, a precipitate forms and appears as a pale yellow gelatinous substance that is highly viscous in substance. It is this viscous substance that is then subjected to the drying process and may be used medicinally once in powder form.

To establish the preferred embodied content of the dried extract in the powder, the following procedure is recommended. Letting x represent the weight of the dried extract and y representing the weight of the added Aerosil 200 powder. Thus, the real weight of the extract is X−Y=Z. Z=the real weight of the extract Thus, in order to obtain the content of the active compound by extract, the untreated total extract needed for 1000 grams of the active compound must be determined as follows. Therefore, 1. 100 grams=z*100/1000

II. The total extract of amino compounds: Z with respect to the active compound used for 1,000 grams of active compound for 100 grams=z*100 or 1000=a% with respect to untreated total for z grams of untreated total extract.

III. Z grams of total extract of the amino compounds:

for 100 grams, z=z*100/z=b%

The dried extracts may then be used medicinally in capsule form. In a preferred embodiment, the capsules are filled according to the following process:

Dried extract 300.00 grains

Aerosil 200 qsqf 500.00 grams

UPF Capsule DT size: 300 mg.
upon filling the capsule with the dried extract, the extract may be used medicinally according to the following dosages:

A. For patients having a CD4 count <250:

Two 300 mg capsules should be administered three times a day (TID) for approximately six months (i.e. 3×2 capsules of 300 mg. a day for approximately 6 months).

B. For patients having CD4 count >250:

One 300 mg capsule should be administered three times a day (TID) for approximately six months (i.e. 3×1) capsules/day for approximately 6 months).

I claim:

1. The substantially purified extract of a plant root from the family Annonaceae and the genus Uvaria wherein the species is *brevistipitata*.

2. A method for the treatment of AIDS comprising administering to a patient in need thereof a substantially pure root extract taken from the plant family Annonaceae and the genus Uvaria in an amount effective to promote remission of said AIDS, in a pharmaceutically acceptable carrier therefor.

3. The method of claim 2 wherein the species is *brevistipitata*.

4. A method for treating immunodeficiency diseases including HIV, Hepatitis A and B, Herpes Simplex Viruses, and Lupus, comprising administering to a patient in need thereof an effective amount of a substantially pure root extract of a plant from the family Annonaceae and the species *Uvaria brevistipitata* comprising the steps of:

providing a substantially purified Annonaceae root extract from the species *Uvaria brevistipitata*.

5. The method of claim 4 wherein providing a substantially pure Annonaceae root extract from a species of Uvaria further comprises the steps of:

grinding a quantity of root from a *Uvaria brevistipitata* plant;

boiling said quantity of root in distilled water to make a solution;

cooling said solution to form a total extract solution;

adding a quantity of activated carbon to said total extract solution;

filtering said total extract solution to form a total extract filtrate;

distilling said total extract filtrate;

mixing a quantity of methanol with said filtrate to form a methanol/precipitate solution;

filtering said methanol/precipitate solution to recover a purified root extract;

collecting said purified root extract; and, drying said root extract.

6. The method of claim 4 wherein administering said root extract to said treatment subject further comprises the steps of:

administering a therapeutic dosage based on a range of dosages from 0.608 milligrams per kilogram per day to 0.68526 grams per kilogram per day;

providing a quantity of said root extract in accordance with said therapeutic dosage; and ingesting said quantity of said root extract.

7. A process for obtaining substantially pure root extract plant from the family Annonaceae and the genus Uvaria comprising the steps of:

providing a quantity of root from an Annonaceae plant, genus Uvaria;

grinding a quantity of root from a *Uvaria brevistipitata* Plant;

boiling said quantity of root in distilled water to make a solution;

cooling said solution to form a total extract solution;

adding a quantity of activated carbon to said total extract solution;

filtering said total extract solution to form a total extract filtrate;

distilling said total extract filtrate;

mixing a quantity of methanol with said total extract filtrate to form a methanol/filtrate solution;

filtering said methanol/filtrate solution to collect a purified root extract;

collecting said purified root extract; and, drying said root extract.

8. The process of claim 7 wherein grinding a quantity of root from a *Uvaria brevistipitata* plant further comprises the steps of:

providing a conventional mill;

reducing said root to a pulpy consistency; and, disrupting plant cell walls of said root.

9. The process of claim 7 wherein boiling said quantity of root in distilled water to make a solution further comprises the step of:

boiling said quantity of root for thirty minutes.

10. The process of claim 7 wherein adding a quantity of activated carbon to said total extract solution further comprises the step of:

providing 100 grams of activated carbon.

11. The process of claim 7 wherein filtering said total extract solution to form a total extract filtrate further comprises the step of:

providing a filter element, said filter element comprising one member taken from the following group: cotton gauze, filter paper, or cotton balls.

12. The process of claim 7 wherein the steps of distilling said total extract, filtering said total extract to form a total extract filtrate, mixing a quantity of methanol with said total extract filtrate to form a methanol/filtrate solution, filtering said methanol/filtrate solution to collect a purified root extract on the paper filter, and collecting said purified root extract are repeated.

13. The process of claim 12 wherein the step of adding a drying agent to said root extract further comprises the step of:

providing a quantity of Aerosol 200 brand drying agent.

14. The process of claim 7 wherein the step of drying said root extract further comprises the steps of:

adding a drying agent to said root extract;

grinding said root extract in the presence of said drying agent in a mortar and pestle;

and placing said ground root extract in an oven.

* * * * *

UNITED STATES PATENT AND TRADEMARK OFFICE
CERTIFICATE OF CORRECTION

PATENT NO. : 5,607,673
DATED : March 4, 1997
INVENTOR(S) : Constantin Bashengezi It is certified that error appears in the above-indentified patent and that said Letters Patent is hereby corrected as shown below:

Title page, item [75] "Bukavih": --Bukavu--.
Title page, under abstract [57] line 3 "bevistipitata": --brevistipitata--.
Title page, under abstract [57] line 10 "HIV$_{11B}$" : --HIV$_{111B}$--.
Columm 3 line 22 and 32, "vital" --viral--.
Columm 3 line 41, "transcriptise", --transcriptase--.
Columm 4 lines 21 and 26, "vital" --viral--.

Signed and Sealed this

Twenty-eighth Day of October, 1997

*Attest:*

BRUCE LEHMAN

*Attesting Officer*  *Commissioner of Patents and Trademarks*